| United States Patent [19] | [11] Patent Number: 4,793,977 |
|---|---|
| Morris | [45] Date of Patent: Dec. 27, 1988 |

[54] COLORIMETRIC DETECTOR FOR MONITORING OIL DEGRADATION

[75] Inventor: R. Scott Morris, Fairhaven, Mass.

[73] Assignee: Cape Cod Research, Inc., Buzzards Bay, Mass.

[21] Appl. No.: 36,354

[22] Filed: Apr. 9, 1987

[51] Int. Cl.$^4$ ............................................. G01N 21/80
[52] U.S. Cl. ....................................... 422/55; 422/56; 422/57; 436/61
[58] Field of Search ................... 422/56, 57, 68.11, 55; 436/61, 163

[56] References Cited

U.S. PATENT DOCUMENTS

| 3,544,484 | 12/1970 | Roth | 436/163 |
|---|---|---|---|
| 4,166,804 | 9/1979 | Bleha et al. | 436/163 |
| 4,521,276 | 6/1985 | Witonsky et al. | 436/128 |
| 4,654,309 | 3/1987 | Mlinar et al. | 436/61 |

FOREIGN PATENT DOCUMENTS

| 536901 | 2/1957 | Canada | 436/61 |
|---|---|---|---|
| 689625 | 6/1964 | Canada | 436/61 |
| 963794 | 7/1964 | United Kingdom | 436/61 |

Primary Examiner—Barry S. Richman
Assistant Examiner—Timothy M. McMahon

[57] ABSTRACT

A new and improved on-site method for protecting an internal combustion engine in the field for maximizing service time by determining the change point of the lubricating oil. The on-site method utilizes a new colorimetric method and apparatus which serves as an indicator of the amount of acid build-up in the lubrication oil. The apparatus is a test strip formed from a polymeric matrix comprised of ion-rich domains known as an ionomer. A dye is bonded to the ion-rich domains and then activated by dipping the test strip in a basic solution.

6 Claims, No Drawings

COLORIMETRIC DETECTOR FOR MONITORING OIL DEGRADATION

TECHNICAL FIELD

This invention relates to the monitoring of the degradation of oil and is particularly adaptable for monitoring the degradation of lubricating oil such as that utilized in internal combustion engines.

Although the invention could be applied to any new or used oil including but not limited to cutting oils, rust proofing oils, and oils used for heat or momentum transfer, it was particularly developed to solve a problem associated with lubricating oil used in the internal combustion engine. As is well known, engine manufacturers suggest to the engine operator the intervals at which the lubricating oil should be changed. These suggested periods are based on figures which make assumptions about operating factors such as fuel quality, engine loading, and operating environment. While these suggested periods are based on figures that would include average operating conditions, there are a large number of operators whose operating conditions do not fall within the parameters of the engine manufacturer. For example, a diesel tug boat operator using a diesel fuel containing excessively high levels of sulfur may suffer severe engine damage well before the time the lubricating oil would normally be changed. At the other end of the spectrum, a driver may continuously drive his automobile under conditions whereby the oil is not even close to the degradation requiring that it be changed when the automobile reaches the number of miles at which the manufacturer suggests that oil be changed. As will be appreciated, there are significant warranty problems to the engine manufacturer associated with changing the oil. Additionally, millions of gallons of oil are wasted because engine oil is changed when the oil remains very acceptable.

BACKGROUND OF THE INVENTION

The art has long sought simple, economical, and effective means for determining the condition of oils. It has long been recognized that the degradation of oils involves the oxidation of the oil's various components. This process involves chemical changes in the composition of the oil leading to an increase ultimately in the acidity of the oil. Another factor is the contamination of the oil with water, acid and sludge which result primarily from piston ring and valve guide blow-by. Together these two factors ultimately produce acidic oil which should be changed.

There is not available, however, a satisfactory monitoring apparatus which will monitor the engine oil to determine when the oil has degraded sufficiently to the point where the oil should be changed. So far as is known, the usual prior art method for testing the lubrication oil has consisted of obtaining a sample of the oil and transporting this sample to a laboratory for analysis. While such a method can correctly analyze the oil to determine numerous art recognized factors, such as flash point, pour point, ppm of wear metals, viscosity, sulfated ash content, TBN and TAN, the time delays involved in obtaining results make this method unsatisfactory for determining oil change times, particularly when the engine is located at a remote location from the laboratory.

One standard method for determining the acidity of oil is set forth in the American Society of Testing Materials Standard Test Method D 974. This is also a standard of the Institute of Petroleum under the designation IP 139. This titration method has been widely used to indicate the relative changes that occur in an oil during use under oxidizing conditions and reports these changes in terms of relative changes in neutralization numbers known as the Total Acid Number (TAN) and the Total Base Number (TBN). Compounded engine oils can and usually have both acid and base numbers in this test.

The field of this invention is the detection of the formation of organic acids during the degradation of a lubricant. The kind of detection involved is colorimetric reaction produced by a chromogen the color change of which depends on the buildup of organic acids within the lubricant. Such detectors can be qualitatitive, semi-qualitatitive, or quantitative, and can be read with standard reflectance spectrophotometers, or visually by the eye using color comparison standards. Remote optical sensing of degradation of oil within an operating machine is feasible through the use of a light source and detectors connected via light fibers to the colorimetric detector of this invention. Optical techniques of this type are illustrated in Heitzman U.S. Pat. No. 4,557,900. The invention here relates to the novel chemistry of the detector, and its method of preparation and use.

The subject invention provides a method and apparatus for directly monitoring the corrosive tendency of the oil through visual observations of the changes in color and fluorescence of dyed and chemically treated polymer matrices which have been placed in contact with the oil to be monitored. The method does not require a laboratory or sophisticated chemical equipment, training or skills. The method can be used both as an indicator that the oil should be changed and as a basis to determine, in the field, whether or not a lubricating oil is the wrong type for the engine. With the present invention, mere guesswork is not involved in determining the precise point when a lubricating oil should be changed.

SUMMARY OF THE INVENTION

This invention is based on the discovery that a highly sensitive colorimetric detector can be prepared whose color changes can be empirically related to the effects observed in operating engines as oils degrade under prolonged use. These results are also observed even after the detector of this invention has experienced continuous contact with 100° C. lubricating oil for more than a month.

This invention can be prepared from three chemical reagents: a polymeric matrix, one or more indicator dyes, and an activation treatment involving an application of an aqueous solution of base.

Ionomers are the preferred materials for forming the polymeric matrix. Ionomers are polymers whose structure can be broadly described as that of a microphase-separated system in which a polymer matrix of low ionic content is interspersed with ion-rich domains. These ion-rich domains are believed to be associated with a number of tightly bound water molecules. Preferred ionomers are optically transparent polymer matrixes based on ethylene, styrene, tetrafluoroethylene, and/or carboxylated phenylated polyphenylene groups. Ionomers containing sulfonic, carboxyl and/or quarternary ammonium sites are preferred for their thermal and chemical stability.

The preferred choices of dyes are dictated by the particular choice of ionomer as well as by the optical, chemical and physical properties of the dye. Cationic dyes require ionomers containing negative fixed ion-exchange sites. Anionic dyes require ionomers containing positive fixed sites. Preferred indicator dyes for monitoring oil degradation are those which change color within the pH range of 3.0 to 10.4. Dyes which change color from pH 8.4 to 10.4 serve to warn the operator of loss of antioxidants and buffers from the composition of the oil. Dyes which change color from pH 8.4 to 4.0 alert the operator to the need to change the oil. Dyes which change color below pH 4.0 warn of an unsafe condition. It is feasible and often desirable to utilize more than one dye and thus follow the degradation of the oil by following the changes in colors which result as the acidity of the oil rises during use. For applications involving higher temperatures and long periods of contact between the detector and the oil, it is preferred to select dyes whose chemical structures are better able to resist oxidation and thermal degradation.

Said ionomers and said dyes are reacted together to produce chromogens by soaking said ionomer in a solution of said dye(s). The use of a saturated solution is desirable; however, lower concentrations than the saturation solution may be used. The solvent is not critical; however, ketones such as acetone and methylethyl ketone are preferred because they are subsequently easily removed by evaporation.

In the next and final step, the dyed ionomer matrix is soaked in strong base. Although not known for certainty, the base is believed to become associated with the water of hydration associated with the bound sites in the ionomer. The observed effect is to convert the dye(s) to the color associated with their high pH form. Following treatment with base, the detectors are air dried.

The detectors may be used immediately as prepared or may be stored in air or oil for months prior to use. Placing the detector in an organic oil which has been degraded by use produces a color change and a change in the level of fluorescence of the said detector. These changes can be detected inexpensively using the naked eye and an ultraviolet light source. More precise quantitative measurements of these changes could be accomplished using state-of-the-art spectrophotometers and/or spectrofluoromometers. Remote and continuous changes in the acid level of stagnant or flowing oil can be achieved according to this invention by use of fiber optic cables between an appropriate measurement device and the treated ionomer. In this configuration, the light may be either reflected or absorbed by the ionomer and said ionomer must be in physical contact with the oil sample to be measured.

The use of changes in light absorption of dyes covalently bound to ionomers to optically monitor the acidity of an aqueous solution is well known. (Peterson et al., Analytical Chemistry, vol. 52, 1980, pp 864-869.) However, the detector according to this invention permits monitoring acid concentrations in organic oils which contain essentially no ions and very little water.

The technical basis of the present invention can be more fully understood from the following experimental examples.

EXAMPLE 1

Five cationic dyes were purchased from the Aldrich Chemical Co., Milwaukee, WI. Each of these dyes was dissolved in acetone to form a dilute solution. Pieces of clear ionomer film made of perfluorosulfonic acid polymers (Dupont's Nafion ™ 117 perfluorinated membrane in hydrogen ion form) were immersed in these solutions until the films took on the color of the solutions in which they were immersed. Said dyed films were then soaked for 15 seconds in 0.5M NaOH and air dried.

These detectors were then tested by sequentially immersing them into hot (100° C.) fresh lubricating oil and then into hot (100° C.) acidic lubricating oil with a TAN of more than 2.5. No color changes were observed for the dyed films soaked in the fresh oil over a period of days. However, surprisingly an almost immediate color change took place when said prepared films were soaked in the hot acidic lubricating oil. The dyes used and the color changes observed are listed below:

| Cationic Dye | Film Color Of Dye When Immersed In | |
| --- | --- | --- |
| | Fresh Oil | Acidic Oil |
| Acridine Orange | Yellow | Orange |
| Methylene Blue | Blue | Green |
| Methyl Orange | Red | Yellow |
| Dichlorofluorescein | Pale Yellow | Orange |
| Bromophenol Blue | Blue | Yellow Green |

EXAMPLE 2

Two common anionic dyes, Mordant Orange 1 and 4,4 Bis (4 amino-1 naphthylazo 2,2 stilbene disulfonic acid), were purchased from Aldrich Chemical Company and dissolved in acetone. Ionomers consisting of polyethylene backbones supporting quarternary ammonium groups (RAI Research's R 4025 and ADM 4000) were soaked in these solutions until the ionomer assumed the color of the dye. These treated ionomers were air dried and then soaked for 15 seconds in 0.5M NaOH. These treated membranes were air dried and tested by immersion in fresh lubricating oil and acidic oil.

The results were similar to those of Example 1. Immersion in fresh oil produced no change in color while immersion in acidic oil produced an immediate color change which was readily observable to the naked eye.

EXAMPLE 3

Example 1 was repeated with other ionomers containing sites suitable for binding cations. These ionomers were physically in the form of films and in the form of macroporous beads. The results of these tests closely paralleled those found in Example 1 even though the ionomers were chosen from very different chemical families. Ionomers tested included sulfonated polystyrene crosslinked with DVB (Rohm and Haas), higher molecular weights of perfluorosulfonic acid (Dupont's Nafion ™ 325, 423, and 901) and sulfonated styrene grafted onto polyethylene (RAI Research Corporation, Hauppauge, NY).

EXAMPLE 4

One 2 cm$^2$ piece of Nafion ™ 117 was treated with acridine orange dissolved in acetone while a second piece was treated with 2'7' dichlorofluorescein. Both films were air dried and then soaked in 0.5M NaOH; this gave each film a yellow color. Each was placed under a hand-held ultraviolet (UV) light source and both fluoresced vigorously. Each was then soaked in hot fresh lubricating oil for several days, wiped clean of residual oil and again placed under the UV lamp. Again, each fluoresced vigorously. Finally, each treated film was placed in acidic oil with a TAN of less than 2.5. After 15 minutes, the films were removed from the acidic oil, wiped clean and tested with the UV lamp. The acridine orange film had changed color to orange and yielded no fluorescence under the UV lamp. The dichlorofluorescein dyed film also had become orange and also did not fluoresce.

EXAMPLE 5

The colorimetric detector was prepared according to Example 1 with the addition that two of said cationic dyes, acridine orange and bromophenol blue, were simultaneously dissolved in acetone and the resulting solution used to dye the ionomer film. Said dyed ionomer film was pretreated by soaking it in 0.5M NaOH for fifteen minutes. The resulting detector was light green in color.

Lubricating oil was tested in various engines under various conditions. After engine testing, oil samples were contacted with said colorimetric detector at 100° C. for twenty minutes. The following color changes were then observed with the naked eye.

| Engine Test Condition | Observed Color Change |
|---|---|
| New oil | None |
| Mildly abused oil, 2000 miles | Tan |
| Truck oil, 5000 miles use | Light Brown |
| Turbocharge oil, 5000 miles use | Light Brown |
| Abused oil, 10,000 miles use | Dark Brown |

These changes were used as the basis for a color chart for determining the point at which the lubricating oil should be changed.

While only a limited number of embodiments of the present invention are disclosed and described herein, it will be readily apparent to persons skilled in the art that numerous changes and modifications may be made without departing from the scope of the invention. Accordingly, the foregoing disclosure and description thereof are for illustrative purposes only and do not in any way limit the invention which is defined only by the claims which follow.

What is claimed is:

1. A colorimetric detector for determining the corrosive nature of an oil, over a wide temperature range and in operating internal combustion engines comprising:
    a. a polymeric matrix comprised of ion-rich domains, chemically bound water and a plurality of hydrophobic domains
    b. ionic indicator dyes covalently bonded to the ion-rich domains in said matrix and which dyes have a net charge opposite to that of said matrix
    c. a basic compound bound to said matrix.

2. The detector of claim 1 in which said polymeric matrix is selected from the group consisting of ethylene, styrene, tetrafluoroethylene, and carboxylated phenylated phenylene backbones (and) with covalently bound sulfonic or quarternary ammonium groups.

3. A detector of claim 1 wherein said base compound is selected from the group consisting of sodium hydroxide, potassium hydroxide, sodium carbonate, potassium carbonate, ammonium hydroxide, ethylamine or diphenylguanidine.

4. A detector of claim 1 wherein the said polymeric matrix forms a solid support for the detector, and forms a reaction zone where corrosive materials from the oil can freely react with said indicator dye within the polymer matrix.

5. The detector of claim 1 in which said ionic dyes are selected from the group consisting of dyes which change color within a pH range of 3.0 and 11.0.

6. The detector of claim 1 in which said ionic dyes are selected from the group consisting of dyes which change fluorescence with a pH range of 3.0 and 11.0.

* * * * *